United States Patent [19]

Haworth et al.

[11] Patent Number: 5,747,491
[45] Date of Patent: May 5, 1998

[54] MORPHOLINE DERIVATIVES AND THEIR USE AS ANTAGONISTS OF TACHIKININS

[75] Inventors: Karen Elizabeth Haworth; Eileen Mary Seward, both of Bishops Stortford; Christopher John Swain, Duxford; Martin Richard Teall, Bishops Stortford, all of United Kingdom

[73] Assignee: Merck Sharp & Dohme Ltd., Hoddesdon, England

[21] Appl. No.: 737,035

[22] PCT Filed: May 1, 1995

[86] PCT No.: PCT/GB95/00983

§ 371 Date: Nov. 1, 1996

§ 102(e) Date: Nov. 1, 1996

[87] PCT Pub. No.: WO95/30674

PCT Pub. Date: Nov. 16, 1995

[30] Foreign Application Priority Data

May 5, 1994 [GB] United Kingdom ............ 9408960
May 5, 1994 [GB] United Kingdom ............ 9408963

[51] Int. Cl.$^6$ .............. A61K 31/535; C07D 413/06
[52] U.S. Cl. ............ 514/236.2; 514/235.8; 544/132; 544/139
[58] Field of Search ................ 544/139, 132; 514/235.8, 236.2

[56] References Cited

U.S. PATENT DOCUMENTS 5,512,570 4/1996 Dorn et al. ............ 514/236.2

FOREIGN PATENT DOCUMENTS

| 0 577 394 | 1/1994 | European Pat. Off. . |
| WO 94/19323 | 9/1994 | WIPO . |
| WO 95/16679 | 6/1995 | WIPO . |
| WO 95/18124 | 7/1995 | WIPO . |

*Primary Examiner*—Robert W. Ramsuer
*Attorney, Agent, or Firm*—J. Eric Thies; David L. Rose

[57] ABSTRACT

The present invention relates to compounds of formula (I): wherein X is N or CH; and pharmaceutically acceptable salts and prodrugs thereof. The compounds are of particular use in the treatment of pain, inflammation, migraine and emesis.

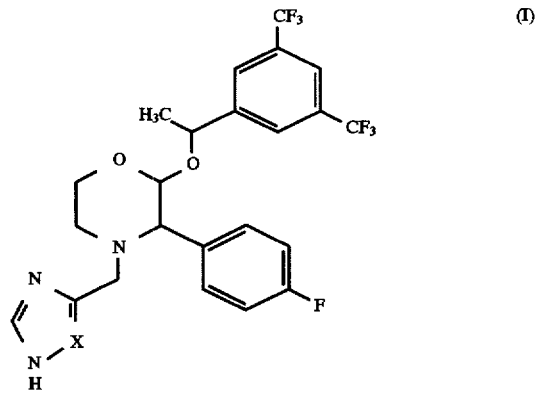

7 Claims, No Drawings

MORPHOLINE DERIVATIVES AND THEIR USE AS ANTAGONISTS OF TACHIKININS

This application is a 371 of PCT/GB95/00983 filed May 1, 1995.

This invention relates to novel compounds which are useful as tachykinin antagonists, particularly as antagonists of substance P. More particularly, the invention relates to morpholine derivatives, processes for their preparation, pharmaceutical compositions containing them, and their use in medicine.

The tachykinins are a group of naturally occurring peptides found widely distributed throughout mammalian tissues, both within the central nervous system and in peripheral nervous and circulatory systems.

At present, there are three known mammalian tachykinins referred to as substance P, neurokinin A (NKA, substance K, neuromedin L) and neurokinin B (NKB, neuromedin K) (for review see J. E. Maggio, Peptides (1985) 6(suppl. 3), 237–242). The current nomenclature designates the three tachykinin receptors mediating the biological actions of substance P, NKA and NKB as the $NK_1$, $NK_2$ and $NK_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, J. Auton. Pharmacol. (1993) 13, 23–93.

For instance, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Synmposium 91, 13–34 (published by Pitman) and Otsuka and Yanagisawa, "Does Substance P Act as a Pain Transmitter?" TIPS (1987) 8, 506–510], specifically in the transmission of pain in migraine (B. E. B. Sandberg et al, J. Med. Chem, (1982) 25, 1009) and in arthritis [Levine et al in Science (1984) 226, 547–549]. Tachykinins have also been implicated in gastrointestinal (GI) disorders and diseases of the GI tract such as inflammatory bowel disease [Mantyh et al in Neuroscience (1988) 25(3), 817–37 and D. Regoli in "Trends in Cluster Headache" Ed. Sicuteri et al Elsevier Scientific Publishers, Amsterdam (1987) page 85)] and emesis [F. D. Tattersall et al, Eur. J. Pharmacol., (1993) 250, R5–R6]. It is also hypothesised that there is a neurogenic mechanism for arthritis in which substance P may play a role [Kidd et al "A Neurogenic Mechanism for Symmetrical Arthritis" in The Lancet, 11 Nov. 1989 and Grönblad et al, "Neuropeptides in Synovium of Patients with Rheumatoid Arthritis and Osteoarthritis" in J. Rheumatol. (1988) 15(12), 1807–10]. Therefore, substance P is believed to be involved in the inflammatory response in diseases such as rheumatoid arthritis and osteoarthritis, and fibrositis [O'Byrne et al, Arthritis and Rheumatism (1990) 33, 1023–8]. Other disease areas where tachykinin antagonists are believed to be useful are allergic conditions [Hamelet et al, Can. J. Pharmacol. Physiol. (1988) 66, 1361–7], immunoregulation [Lotz et al, Science (1988) 241, 1218–21 and Kimball et al, J. Immunol. (1988) 141(10), 3564–9] vasodilation, bronchospasm, reflex or neuronal control of the viscera [Mantyh et al, Proc. Natl. Acad. Sci., USA (1988) 85, 3235–9] and, possibly by arresting or slowing β-amyloid-mediated neurodegenerative changes [Yankner et al, Science (1990) 250, 279–82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et al, Cancer Research (1992) 52, 4554–7].

Substance P may also play a role in demyelinating diseases such as multiple sclerosis and amyotrophic lateral sclerosis [J. Luber-Narod et al, poster C.I.N.P. XVIIIth Congress, 28th Jun.–2nd Jul. 1992], and in disorders of bladder function such as bladder detrusor hyper-reflexia (The Lancet, 16th May 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus (European patent specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

European patent specification no. 0 577 394 (published 5th Jan. 1994) discloses morpholine and thiomorpholine tachykinin receptor antagonists of the general formula

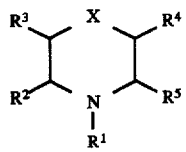

wherein $R^1$ is a large variety of substituents;

$R^2$ and $R^3$ are inter alia hydrogen;

$R^4$ is inter alia

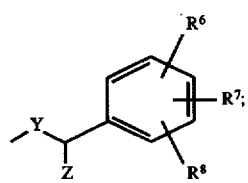

$R^5$ is inter alia optionally substituted phenyl;

$R^6$, $R^7$ and $R^8$ are a variety of substituents;

X is O, S, SO or $SO_2$;

Y is inter alia O; and

Z is hydrogen or $C_{1-4}$ alkyl.

We have found the compounds of the present invention to be particularly potent and useful antagonists of tachykinins, especially of substance P.

It is desirable that compounds may be administered orally and by injection. Certain compounds have now been discovered which act as potent non-peptide tachykinin antagonists and which, by virtue of their advantageous aqueous solubility, are particularly easily formulated for administration by both the oral and injection routes, for example, in aqueous media.

The present invention provides compounds which have the formula (I):

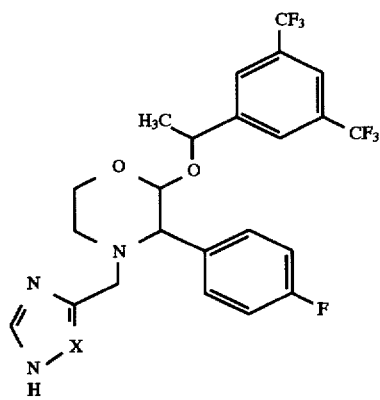

(I)

where

X is N or CH;

and pharmaceutically acceptable salts and prodrugs thereof

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of a compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety.

The compounds according to the invention have three asymmetric centres, and may accordingly exist both as enantiomers and as diastereoisomers. It is to be understood that all such isomers and mixtures thereof are encompassed within the scope of the present invention.

The preferred compounds of formula (I) will have the 2- and 3-substituent cis and the preferred stereochemistry at the 2-position is that possessed by the compounds of Examples 1 and 2 (i.e. 2-(R)-), the preferred stereochemistry of the 3-position is that possessed by the compounds of Examples 1 and 2 (i.e. 3-(S)), and the stereochemistry of the carbon to which the α-methyl group is attached is preferably (R), i.e. compounds of the formula (Ia):

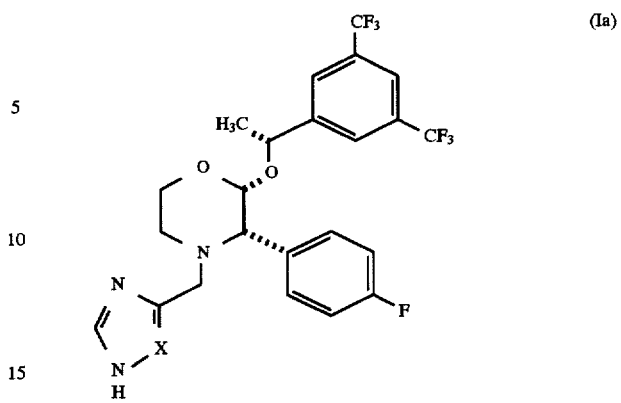

(Ia)

The present invention includes within its scope prodrugs of the compounds of formula (I) above. In general, such prodrugs will be functional derivatives of the compounds of formula (I) which are readily convertible in vivo into the required compounds of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

Thus, for example, certain preferred prodrugs may not be antagonists of tachykinin, particularly substance P, activity to any significant extent (or not at all). Such compounds, however, are still advantageous in treating the various conditions described herein, especially where an injectable formulation is preferred.

The advantages of a prodrug may lie in its physical properties, such as enhanced water solubility for parenteral administration compared with the parent drug, or it may enhance absorption from the digestive tract, or it may enhance drug stability for long-term storage. Ideally a prodrug will improve the overall efficacy of a parent drug, for example, through the reduction of toxicity and unwanted effects of drugs by controlling their absorption, blood levels, metabolism, distribution and cellular uptake.

It will be appreciated that in the compounds of formula (I) above, the 1,2,4-triazol-3-yl or 1,3-imidazol-4-yl group may be derivatized to give a prodrug of the compounds of the present invention.

Suitable prodrug derivatives include:

(a) —(CHR$^{10}$)$_n$—PO(OH)O$^-$.M$^+$;

(b) —(CHR$^{10}$)$_n$—PO(O$^-$)$_2$.2M$^+$;

(c) —(CHR$^{10}$)$_n$—PO(O$^-$)$_2$.D$^{2+}$;

(d) —(CHR$^{10}$)$_n$—SO$_3^-$.M$^+$;

(e) —COCH$_2$CH$_2$CO$_2^-$.M$^+$;

(f) —COH;

(g) —CO(CH$_2$)$_n$N(R$^{10}$)$_2$; and (h) —(CH(R$^{10}$)O)$_n$—COR$^{11}$, wherein n is zero or 1;

M$^+$ is a pharmaceutically acceptable monovalent counterion;

$D^{2+}$ is a pharmaceutically acceptable divalent counterion;
$R^{10}$ is hydrogen or $C_{1-3}$alkyl; and
$R^{11}$ is a group selected from —$O(CH_2)_2NH_3^+.M^-$; —$O(CH_2)_2NH_2(R^{12})^+.M^{31}$; —$OCH_2CO_2^-.M^+$; —$OCH(CO_2^-.M^+)CH_2CO_2^-.M^+$; —$OCH_2CH(NH_3^+)CO_2^-$; —$OC(CO_2^-.M^+)(CH_2CO_2^-.M^+)_2$; and

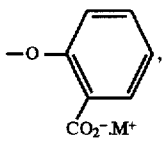

in which $M^-$ is a pharmaceutically acceptable monovalent counterion, and $R^{12}$ is hydrogen, $C_{1-4}$alkyl or $C_{2-4}$alkyl substituted by a hydroxyl or $C_{1-4}$alkoxy group.

Particularly preferred prodrug derivatives are:

(a) —$(CHR^{10})_n$—$PO(OH)O^-.M^+$;
(b) —$(CHR^{10})_n$—$PO(O^-)_2.2M^+$;
(c) —$(CHR^{10})_n$—$PO(O^-)_2.D^{2+}$; especially where n is zero.

The term "parent molecule", "parent compound" or "parent drug" refers to the biologically active entity that is released via enzymatic action of a metabolic or catabolic process, or via a chemical process following administration of the prodrug. The parent compound may also be the starting material for the preparation of its corresponding prodrug.

While all of the usual routes of administration are useful with the above prodrugs, the preferred routes of administration are oral and intravenous. After gastrointestinal absorption or intravenous administration, the prodrugs are hydrolyzed or otherwise cleaved in vivo to the corresponding parent compound of formula (I), or a pharmaceutically acceptable salt thereof.

Examples of negative monovalent counterions defined herein as "$M^-$" include acetate, adipate, benzoate, benzenesulfonate, bisulfate, butyrate, camphorate, camphorsulfonate, citrate, ethanesulfonate, fumarate, hemisulfate, 2-hydroxyethylsulfonate, heptanoate, hexanoate, hydrochloride, hydrobromide, hydroiodide, lactate, malate, maleate, methanesulfonate, 2-naphthalenesulfonate, oxalate, pamoate, persulfate, picrate, pivalate, propionate, salicylate, stearate, succinate, sulfate, tartrate, tosylate (p-toluenesulfonate), and undecanoate.

Base salts (which are pharmaceutically acceptable monovalent cations defined herein as "$M^+$" or pharmaceutically acceptable divalent cations defined herein as "$D^{2+}$", if appropriate) include ammonium salts, alkali metal salts such as sodium, lithium and potassium salts, alkaline earth metal salts such as aluminium, calcium and magnesium salts, salts with organic bases such as dicyclohexylamine salts, N-methyl-D-glucamine, and salts with amino acids such as arginine, lysine, ornithine, and so forth. If $M^+$ is a monovalent cation, it is recognised that if the definition $2M^+$ is present, each of $M^+$ may be the same or different. In addition, it is similarly recognised that if the definition $2M^+$ is present, a divalent cation $D^{2+}$ may instead be present. Also, the basic nitrogen-containing groups may be quaternized with such agents as: lower alkyl halides, such as methyl, ethyl, propyl, and butyl chlorides, bromides and iodides; dialkyl sulfates like dimethyl, diethyl and dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope solvates of the compounds of formula (I) and salts thereof, for example, hydrates.

The present invention further provides pharmaceutical compositions comprising a compound of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention.

The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example gylcerol or glucose, to adjust the tonicity of the emulsion. Suitable emulsions will typically contain up to 20% oil, for example, between 5 and 20%. The fat emulsion will preferably comprise fat droplets between 0.1 and 1.0 µm, particularly 0.1 and 0.5 µm, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

These may include disorders of the central nervous system such as anxiety, depression, psychosis and schizophrenia; epilepsy; neurodegenerative disorders such as dementia, including AIDS related dementia, senile dementia of the Alzheimer type, Alzheimer's disease and Down's syndrome; demyelinating diseases such as multiple sclerosis (MS) and amyotrophic lateral sclerosis (ALS; Lou Gehrig's disease) and other neuropathological disorders such as peripheral neuropathy, for example AIDS related neuropathy, diabetic and chemotherapy-induced neuropathy, and postherpetic and other neuralgias; neuronal damage, such as cerebralischemic damage and cerebral edema in cerebrovascular disorders; small cell carcinomas such as small cell lung cancer; respiratory diseases, particularly those associated with excess mucus secretion such as chronic obstructive airways disease, bronchopneumonia, chronic bronchitis, asthma, and bronchospasm; airways diseases modulated by neurogenic inflammation; diseases characterised by neurogenic mucus secretion, such as cystic fibrosis; diseases associated with decreased glandular secretions, including lacrimation, such as Sjogren's syndrome, hyperlipoproteinemias IV and V, hemocromatosis, sarcoidosis, and amyloidosis; inflammatory diseases such as inflammatory bowel disease, psoriasis, fibrositis, ocular inflammation, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, dry eye syndrome, and the like; ophthalmic conditions associated with cell proliferation such as proliferative vitreoretinopathy; cutaneous diseases such as contact dermatitis, atopic dermatitis, urticaria, and other eczematoid dermatitis; addiction disorders including the withdrawal response produced by chronic treatment with, or abuse of, drugs such as benzodiazepines, opiates, cocaine, alcohol and nicotine; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosus; gastrointestinal (GI) disorders and diseases of the GI tract such as disorders associated with the neuronal control of viscera, ulcerative colitis, Crohn's disease, irritable bowel syndrome and emesis, including acute, delayed, post-operative, late phase or anticipatory emesis such as emesis induced by chemotherapy, radiation, toxins, viral or bacterial infections, pregnancy, vestibular disorders, motion, surgery, migraine, opioid analgesics, and variations in intercranial pressure, in particular, for example, drug or radiation induced emesis or post-operative nausea and vomiting; disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

Hence, the compounds of the present invention may be of use in the treatment of physiological disorders associated with excessive stimulation of tachykinin receptors, especially neurokinin-1 receptors, and as neurokinin-1 antagonists for the control and/or treatment of any of the aforementioned clinical conditions in mammals, including humans.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed, post-operative, late phase or anticipatory emesis, such as emesis or nausea induced by chemotherapy, radiation, toxins, such as metabolic or microbial toxins, viral or bacterial infections, pregnancy, vestibular disorders, motion, mechanical stimulation, gastrointestinal obstruction, reduced gatrointestinal motility, visceral pain, psychological stress or disturbance, high altitude, weightlessness, opioid analgesics, intoxication, resulting for example from consumption of alcohol, surgery, migraine, and variations in intercranial pressure. Most especially, the compounds of formula (I) are of use in the treatment of emesis induced by antineoplastic (cytotonic) agents including those routinely used in cancer chemotherapy.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in "Nausea and Vomiting: Recent Research and Clinical Advances", Eds. J. Kuucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-$HT_3$ antagonist, such as ondansetron, granisetron or tropisetron, or other anti-emetic medicaments, for example, a dopamine antagonist such as metoclopramide or GABAB receptor agonists such as baclofen. Additionally, a compound of formula (I) may be administered in combination with an anti-inflammatory corticosteroid, such as dexamethasone, triamcinolone, triamcinolone acetonide, flunisolide, budesonide, or others such as those disclosed in U.S. Pat. Nos. 2,789,118, 2,990,401, 3,048,581, 3,126,375, 3,929,768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. pharmacol.*, (1993) 250, R5-R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis, headache and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene $D_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-$HT_1$ agonists, especially sumatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an antiinflammatory agent such as a bradykinin receptor antagonist.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compound may be administered on a regimen of 1 to 4 times per day, preferably once or twice per day.

In the treatment-of emesis using an injectable formulation, a suitable dosage level is about 0.001 to 10 mg/kg per day, preferably about 0.005 to 5 mg/kg per day, and especially 0.01 to 1 mg/kg per day. The compound may be administered on a regimen of 1 to 4 times per day, preferably once or twice per day.

It will be appreciated that the amount of the compound of formula (I) required for use in any treatment will vary not only with the particular composition selected but also with the route of administration, the nature of the condition being treated, and the age and condition of the patient, and will ultimately be at the discretion of the attendant physician.

According to a process (A), the compounds of the present invention may be prepared from the compound of formula (II)

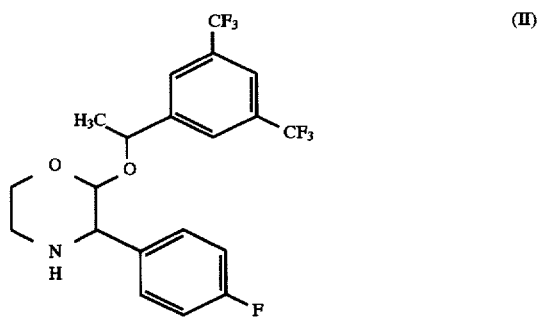

by reaction with a compound of formula (III):

or a protected derivative thereof, wherein X is N or CH, and L is a leaving group such as a halogen atom, for example, chlorine, bromine or iodine or an alkyl- or arylsulphonyloxy group, for example, a mesylate or tosylate group, followed where necessary by deprotection in a conventional manner.

One particularly suitable protecting group for the compounds of formula (III) is the p-toluenesulphonyl group.

This reaction may be performed in conventional manner, for example in an organic solvent such as dimethylformamide in the presence of an acid acceptor such as potassium carbonate.

Alternatively, according to a process (B), the compound of formula (I) in which X is N may be prepared by reaction of an intermediate of formula (II) with a compound of formula (IV)

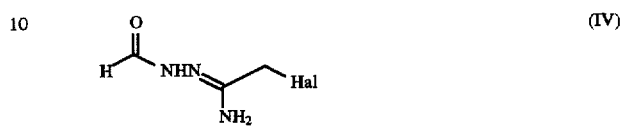

wherein Hal is a halogen atom, for example, bromine, chlorine or iodine, in the presence of a base.

Suitable bases of use in the reaction include alkali metal carbonates such as, for example, potassium carbonate. The reaction is conveniently effected in an anhydrous organic solvent such as, for example, anhydrous dimethylformamide, preferably at elevated temperature, such as between 60° C. and 140° C.

Further details of suitable procedures will be found in the accompanying Examples.

Compounds of formula (III) are commercially available or may be prepared by the procedures described in the accompanying Examples or from commercially available compounds by methods readily apparent to one skilled in the art.

Compounds of formula (IV) may be prepared as described in *J. Med. Chem.*, 27, 849 (1984).

The compounds of the formula (II) may be prepared as shown in the following Scheme:

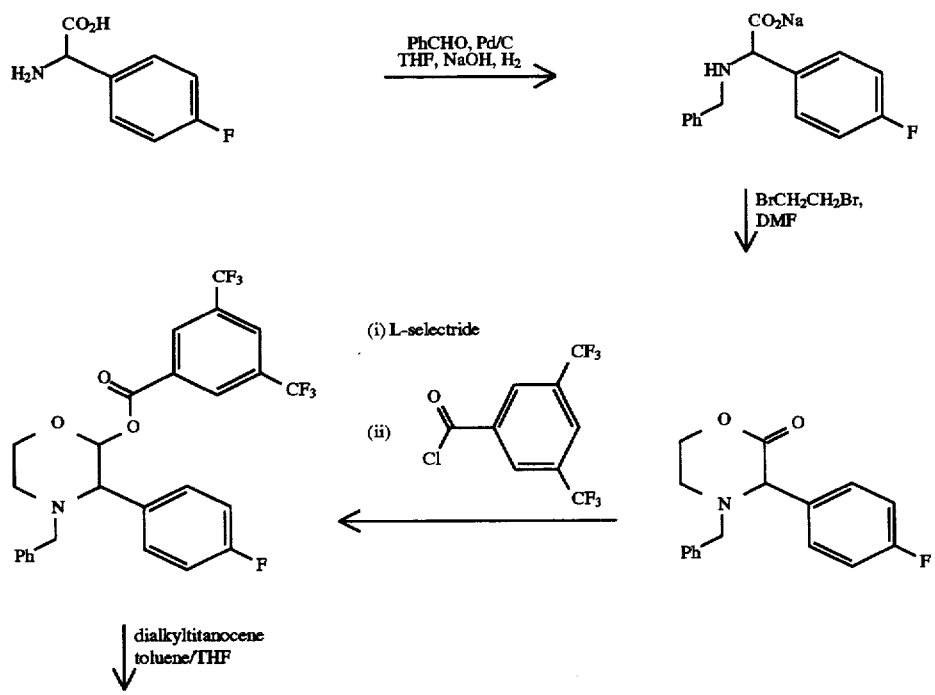

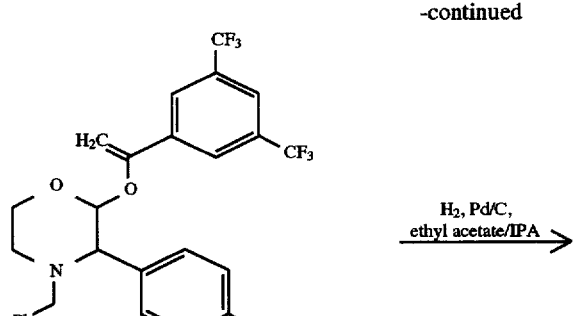

The following references describe methods which may be applied by the skilled worker to the chemical synthesis set forth above once the skilled worker has read the disclosure herein.

(i) D. A. Evans et al., *J. Am. Chem. Soc.*, 112, 4011 (1990).
(ii) Yanagisawa, I. et al., *J. Med. Chem.*, 27 849 (1984).
(iii) Duschinsky, R. et al., *J. Am. Chem. Soc.*, 70, 657 (1948).
(iv) Tebbe F. N. et al., *J. Am. Chem. Soc.*, 100, 3611 (1978).
(v) Petasis, N. A. et al., *J. Am. Chem. Soc.*, 112, 6532 (1990).
(vi) Takai, K. et al., *J. Org. Chem.*, 52, 4412 (1987).

The Examples disclosed herein produce predominantly the preferred isomers. The unfavoured isomers are also produced as minor components. If desired they may be isolated and employed to prepare the various stereoisomers in conventional manner, for example chromatography using an appropriate chiral column. However, the skilled worker will appreciate that although the Examples have been optimized to the production of the preferred isomers, variation in solvent, reagents, chromatography etc can be readily employed to yield the other isomers.

L-Selectride is lithium tri-sec-butylborohydride.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The compounds of the present invention were tested by the methods set out at pages 36 to 39 of International Patent Specification No. WO 93/01165. The compounds were both found to be active with $IC_{50}$ at the NK1 receptor of 0.1 nM.

DESCRIPTION 1

(S)-(4-Fluorophenyl)glycine
Via Chiral Synthesis
Step A 3-(4-Fluorophenyl)acetyl-4-(S)-benzyl-2-oxazolidinone An oven-dried, 1 L 3-necked flask, equipped with a septum, nitrogen inlet, thermometer, and a magnetic stirring bar, was flushed with nitrogen and charged with a solution of 5.09 g (33.0 mmol) of 4-fluorophenylacetic acid in 100 ml of anhydrous ether. The solution was cooled to −10° C. and treated with 5.60 ml (40.0 mmol) of triethylamine followed by 4.30 ml (35.0 mmol) of trimethylacetyl chloride. A white precipitate formed immediately. The resulting mixture was stirred at −10° C. for 40 minutes, then cooled to −78° C.

An oven-dried, 250 ml round bottom flask, equipped with a septum and a magnetic stirring bar, was flushed with nitrogen and charged with a solution of 5.31 g (30.0 mmol) of 4-(S)-benzyl-2-oxazolidinone in 40 ml of dry THF. The solution was stirred in a dry ice/acetone bath for 10 minutes, then 18.8 ml of 1.6M n-butyllithium solution in hexanes was slowly added. After 10 minutes, the lithiated oxazolidinone solution was added, via cannula, to the above mixture in the 3-necked flask. The cooling bath was removed from the resulting mixture and the temperature was allowed to rise to 0° C. The reaction was quenched with 100 ml of saturated aqueous ammonium chloride solution, transferred to a 1 l flask, and the ether and THF were removed in vacuo. The concentrated mixture was partitioned between 300 ml of methylene chloride and 50 ml of water and the layers were separated. The organic layer was washed with 100 ml of 2N aqueous hydrochloric acid solution, 300 ml of saturated aqueous sodium bicarbonate solution, dried over magnesium sulfate and concentrated in vacuo. Flash chromatography on 400 g of silica gel using 3:2 v/v hexanes/ether as the eluant afforded 8.95 g of an oil that slowly solidified on standing. Recrystallisation from 10:1 hexanes/ether afforded 7.89 g (83%) of the title compound as a white solid: mp 64°–66° C. MS (FAB): m/z 314 ($M^+$+H, 100%), 177 (M-ArCH$_2$CO+H, 85%). $^1$H NMR (400 MHz, CDCl$_3$) δ2.76 (1H, dd, J=13.2, 9.2 Hz), 3.26 (dd, J=13.2, 3.2 Hz), 4.16–4.34 (4H, m), 4.65 (1H, m), 7.02–7.33 (9H, m). Analysis Calcd. for $C_{18}H_{16}FNO_3$: C, 69.00; H, 5.15; N, 4.47; F, 6.06; Found: C, 68.86; H, 5.14; N, 4.48; F, 6.08%

Step B 3-((S)-Azido-(4-fluorophenyl))acetyl-4-(S)-benzyl-2-oxazolidinone

An oven-dried, 1 l 3-necked flask, equipped with a septum, nitrogen inlet, thermometer, and a magnetic stirring bar, was flushed with nitrogen and charged with a solution of 58.0 ml of 1M potassium bis(trimethylsilyl)amide solution in toluene and 85 ml of THF and was cooled to −78° C. An oven-dried 250 ml round-bottomed flask, equipped with a septum and a magnetic stirring bar, was flushed with nitrogen and charged with a solution of 7.20 g (23.0 mmol) of 3-(4-fluorophenyl)acetyl-4-(S)-benzyl-2-oxazolidinone (from Step A) in 40 ml of THF. The acyl oxazolidinone solution was stirred in a dry ice/acetone bath for 10 minutes, then transferred, via cannula, to the potassium bis (trimethylsilyl)amide solution at such a rate that the internal temperature of the mixture was maintained below −70° C. The acyl oxazolidinone flask was rinsed with 15 ml of THF and the rinse was added, via cannula, to the reaction mixture and the resulting mixture was stirred at −78° C. for 30 minutes. An oven-dried, 250 ml round-bottomed flask, equipped with a septum and a magnetic stirring bar, was flushed with nitrogen and charged with a solution of 10.89 g (35.0 mmol) of 2,4,6-triisopropylphenylsulfonyl azide in 40 ml of THF. The azide solution was stirred in a dry ice/acetone bath for 10 minutes, then transferred, via cannula, to the reaction mixture at such a rate that the internal temperature of the mixture was maintained below −70° C. After 2 minutes, the reaction was quenched with 6.0 ml of glacial acetic acid, the cooling bath was removed and the mixture was stirred at room temperature for 18 hours. The quenched reaction mixture was partitioned between 300 ml of ethyl acetate and 300 ml of 50% saturated aqueous sodium bicarbonate solution. The organic layer was separated, dried over magnesium sulfate, and concentrated in vacuo. Flash chromatography on 500 g of silica gel using 2:1 v/v, then 1:1 v/v hexanes/methylene chloride as the eluant afforded 5.45 g (67%) of the title compound as an oil. IR Spectrum (neat, cm$^{-1}$): 2104, 1781, 1702. $^1$H NMR (400 MHz, CDCl$_3$) δ2.86 (1H, dd, J=13.2, 9.6 Hz), 3.40 (1H, dd, J=13.2, 3.2 Hz), 4.09–4.19 (2H, m), 4.62–4.68 (1H, m), 6.14 (1H, s), 7.07–7.47 (9H, m). Analysis Calcd. for C$_{18}$H$_{15}$FN$_4$O$_3$:C 61.01; H, 4.27; N, 15.81; F, 5.36; Found: C, 60.99; H, 4.19; N, 15.80; F, 5.34%

Step C (S)-Azido-(4-fluorophenyl)acetic acid

A solution of 5.40 g (15.2 mmol) of 3-((S)-azido-(4-fluorophenyl)) acetyl-4-(S)-benzyl-2-oxazolidinone (from Step B) in 200 ml of 3:1 v/v THF/water was stirred in an ice bath for 10 minutes. 1.28 g (30.4 mmol) of lithium hydroxide monohydrate was added in one portion and the resulting mixture was stirred cold for 30 minutes. The reaction mixture was partitioned between 100 ml of methylene chloride and 100 ml of 25% saturated aqueous sodium bicarbonate solution and the layers were separated. The aqueous layer was washed with 2×100 ml of methylene chloride and acidified to pH 2 with 2N aqueous hydrochloric acid solution.

The resulting mixture was extracted with 2×100 ml of ethyl acetate; the extracts were combined, washed with 50 ml of saturated aqueous sodium chloride solution, dried over magnesium sulfate, and concentrated in vacuo to afford 2.30 g (77%) of the title compound as an oil that was used in the following step without further purification. IR Spectrum (neat, cm$^{-1}$): 2111, 1724. $^1$H NMR (400 MHz, CDCl$_3$) δ5.06 (1H, s), 7.08–7.45 (4H, m), 8.75 (1H, br s).

Step D (S)-(4-Fluorophenyl)glycine

A mixture of 2.30 g (1 1.8 mmol) of (S)-azido-(4-fluorophenyl)acetic acid (from Step C), 2.50 mg 10% palladium on carbon catalyst and 160 ml 3:1 v/v water/acetic acid was stirred under an atmosphere of hydrogen for 18 hours. The reaction mixture was filtered through Celite and the flask and filter cake were rinsed well with ~1 l of 3:1 v/v water/acetic acid. The filtrate was concentrated in vacuo to about 50 ml of volume. 300 ml of toluene was added and the mixture concentrated to afford a solid. The solid was suspended in 1:1 v/v methanol/ether, filtered and dried to afford 1.99 g (100%) of the title compound. $^1$H NMR (400 MHz, D$_2$O+NaOD) δ3.97 (1H, s), 6.77 (2H, app t, J=8.8 Hz), 7.01 (2H, app t, J=5.6 Hz).

Via Resolution:

Step A'

(4-Fluorophenyl)acetyl chloride

A solution of 150 g (0.974 mol) of 4-(fluorophenyl)acetic acid and 1 ml of N,N-dimethylformamide in 500 ml of toluene at 40° C. was treated with 20 ml of thionyl chloride and heated to 40° C. An additional 61.2 ml of thionyl chloride was added dropwise over 1.5 hours. After the addition, the solution was heated at 50° C. for 1 hour, the solvent was removed in vacuo and the residual oil was distilled at reduced pressure (1.5 mmHg) to afford 150.4 g (89.5%) of the title compound, bp=68°–70° C.

Step B'

Methyl 2-bromo-3-(4-fluorophenyl)acetate

A mixture of 150.4 g (0.872 mol) of 4-(fluorophenyl) acetyl chloride (from Step A') and 174.5 g (1.09 mol) of bromine was irradiated at 40°–50° C. with a quartz lamp for 5 hours. The reaction mixture was added dropwise to 400 ml of methanol and the solution was stirred for 16 hours. The solvent was removed in vacuo and the residual oil was distilled at reduced pressure (1.5 mmHg) to afford 198.5 g (92%) of the title compound, bp=106°–110° C.

Step C'

Methyl (±)-(4-fluorophenyl)glycine

A solution of 24.7 g (0.1 mol) of methyl 2-bromo-2-(4-fluorophenyl) acetate (from Step B') and 2.28 g (0.01 mol) of benzyl triethylammonium chloride in 25 ml of methanol was treated with 6.8 g (0.105 mol) of sodium azide and the resulting mixture was stirred for 20 hours at room temperature. The reaction mixture was filtered; the filtrate was diluted with 50 ml of methanol and hydrogenated in the presence of 0.5 g of 10% Pd/C at 50 psi for 1 hour. The solution was filtered and the solvent removed in vacuo. The residue was partitioned between 10% aqueous sodium carbonate solution and ethyl acetate. The organic phase was washed with water, saturated aqueous sodium chloride solution dried over magnesium sulfate and concentrated in vacuo to afford 9.8 g of the title compound as an oil.

Step D'

Methyl (S)-(4-fluorophenyl)glycinate

A solution of 58.4 g of methyl (±) 4-(fluorophenyl) glycinate (from Step C') in 110 ml of 7:1 v/v ethanol/water was mixed with a solution of 28.6 g (0.0799 mol) of O,O'-(+)-dibenzoyltartaric acid ((+)-DBT) (28.6 g, 0.0799 mol) in 110 ml of 7:1 v/v ethanol:water and the resulting solution was allowed to age at room temperature. Ethyl acetate (220 ml) was added after crystallisation was complete and the resulting mixture was cooled to −20° C. and filtered to afford 32.4 g of methyl (S)-(4-fluorophenyl) glycinate, (+)-DBT salt (ee=93.2%). The mother liquors were concentrated in vacuo and the free base was liberated by partitioning between ethyl acetate and aqueous sodium carbonate solution. A solution of free base, so obtained, in 110 ml of 7:1 v/v ethanol/water was mixed with a solution of 28.6 g (0.0799 mol) of O,O'-(−)-dibenzoyltartaric acid ((−)-DBT) (28.6 g, 0.0799 mol) in 110 ml of 7:1 v/v ethanol:water and the resulting solution was allowed to age at room temperature. Ethyl acetate (220 ml) was added after crysallisation was complete and the resulting mixture was cooled to −20° C. and filtered to afford 47.0 g of methyl (R)-(4-fluorophenyl)glycinate, (−)-DBT salt (ee=75.8%). Recycling of the mother liquors and addition of (+)-DBT gave a second crop of 7.4 g of (S)-(4-fluorophenyl)glycinate, (+)-DBT salt (ee=96.4%). The two crops of the (S)-amino ester (39.8 g) were combined in 200 ml of 7:1 v/v ethanol/water, heated for 30 minutes and cooled to room temperature. Addition of ethyl acetate, cooling, and filtration afforded 31.7 g of (S)-(4-fluorophenyl)glycinate, (+)-DBT salt (ee>98%). Enantiomeric excess was determined by chiral HPLC (Crownpak CR(+) 5% MeOH in aq HClO$_4$pH2 1.5 ml/min 40° C. 200 nm).

A mixture of 17.5 g of (S)-(4-fluorophenyl)glycinate, (+)-DBT salt and 32 ml of 5.5N HCl (32 ml) was heated at reflux for 1.5 hours. The reaction mixture was concentrated in vacuo and the residue was dissolved in 40 ml of water. The aqueous solution was washed (3×30 ml of ethyl acetate) and the layers were separated. The pH of the aqueous layer was adjusted to 7 using ammonium hydroxide and the precipitated solid was filtered to afford 7.4 g of the title compound (ee=98.8%).

DESCRIPTION 2

4-Benzyl-3-(S)- (4-fluorophenyl)-2-morpholinone
Step A

N-Benzyl-(S)-(4-fluorophenyl)glycine

A solution of 1.87 g (11.05 mmol) of (S)-(4-fluorophenyl)-glycine (from Description 1) and 1.12 ml (11.1 mmol) of benzaldehyde in 11.1 ml of 1N aqueous sodium hydroxide solution and 11 ml of methanol at 0° C. was treated with 165 mg (4.4 mmol) of sodium borohydride. The cooling bath was removed and the resulting mixture was stirred at room temperature for 30 minutes. Second portions of benzaldehyde (1.12 ml (11.1 mmol)) and sodium borohydride (165 mg (4.4 mmol)) were added to the reaction mixture and stirring was continued for 1.5 hours. The reaction mixture was partitioned between 100 ml of ether and 50 ml of water and the layers were separated. The aqueous layer was separated and filtered to remove a small amount of insoluble material. The filtrate was acidified to pH 5 with 2N aqueous hydrochloric acid solution and the solid that had precipitated was filtered, rinsed well with water, then ether, and dried to afford 1.95 g of the title compound. $^1$H NMR (400 MHz, D$_2$O+NaOD) δ3.33 (2H, AB q, J=8.4 Hz), 3.85 (1H, s), 6.79–7.16 (4H, m).
Step B 4-Benzyl-3-(S)-(4-fluorophenyl)-2-moropholinone A mixture of 1.95 g (7.5 mmol) of N-benzyl (S)-(4-fluorophenyl) glycine, 3.90 ml (22.5 mmol) of N,N-diisopropyl-ethylamine, 6.50 ml (75.0 mmol) of 1,2-dibromoethane and 40 ml of N,N-dimethylformamide was stirred at 100° C. for 20 hours (dissolution of all solids occurred on warming). The reaction mixture was cooled and concentrated in vacuo. The residue was partitioned between 250 ml of ether and 100 ml of 0.5N potassium hydrogen sulfate solution and the layers were separated. The organic layer was washed with 100 ml of saturated aqueous sodium bicarbonate solution, 3×150 ml of water, dried over magnesium sulfate, and concentrated in vacuo. Flash chromatography on 125 g of silica gel using 3:1 v/v hexanes/ether as the eluant afforded 1.58 g (74%) of the title compound as an oil. $^1$H NMR (400 MHz, CDCl$_3$) δ2.65 (1H, dt, J=3.2, 12.8 Hz), 3.00 (1H, dt, J=12.8, 2.8 Hz), 3.16 (1H, d, J=13.6 Hz), 3.76 (1H, d, J=13.6 Hz), 4.24 (1H, s), 4.37 (1H, dt, J=13.2, 3.2 Hz), 4.54 (1H, dt, J=2.8, 13.2 Hz), 7.07–7.56 (9H, m).

DESCRIPTION 3

4-Benzyl-2 -(R) -(3,5-bis(trifluoromethyl) benzoyloxy)-3-(S)-(4-fluorophenyl)morpholine A solution of 2.67 g (10.0 mmol) of 4-benzyl-3-(S)-(4-fluorophenyl)-2-morpholinone (Description 2) in 40 ml of dry THF was cooled to −78° C. The cold solution was treated with 12.5 ml of 1.0M L-Selectride® solution in THF, maintaining the internal reaction temperature below −70° C. The resulting solution was stirred cold for 45 minutes and the reaction was charged with 3.60 ml(20.0 mmol) of 3,5-bis(trifluoromethyl)benzoyl chloride. The resulting yellow mixture was stirred cold for 30 minutes and the reaction was quenched with 50 ml of saturated aqueous sodium bicarbonate solution. The quenched mixture was partitioned between 300 ml of ether and 50 ml of water and the layers were separated. The organic layer was dried over magnesium sulfate. The aqueous layer was extracted with 300 ml of ether; the extract was dried and combined with the original organic layer. The combined organics were concentrated in vacuo. Flash chromatography on 150 g of silica gel using 37:3 v/v hexanes/ether as the eluant afforded 4.06 g (80%) of the title compound as a solid. $^1$H NMR (200 MHz, CDCl$_3$) δ2.50 (1H, dt, J=3.4, 12.0 Hz), 2.97 (1H, app d, J=12.0 Hz), 2.99 (1H, d, J=13.6 Hz), 3.72–3.79 (1H, m), 3.82 (1H, d, J=2.6 Hz), 4.00 (1H, d, J=13.6 Hz), 4.20 (dt, J=2.4, 11.6 Hz), 6.22 (1H, d, J=2.6 Hz), 7.22–7.37 (7H, m), 7.57 (2H, app d, J=6.8 Hz), 8.07 (1H, s), 8.47 (2H, s). MS (FAB) m/z 528 (M+H, 25%), 270 (100%). Analysis Calcd. for C$_{26}$H$_{20}$F$_7$NO$_3$: C, 59.21; H, 3.82; N, 2.66; F, 25.21. Found: C, 59.06; H, 4.05; N, 2.50; F, 25.18%

DESCRIPTION 4

4-Benzyl-2-(R)-(1-(3,5-bis(trifluoromethyl)ethenyl) ethenyloxy)-3-(S)-(4-fluorophenyl) morpholine
Step A Dimethyl titanocene A solution of 2.49 g (10.0 mmol) of titanocene dichloride in 50 ml of ether in the dark at 0° C. was treated with 17.5 ml of 1.4M methyllithium solution in ether maintaining the internal temperature below 5° C. The resulting yellow/orange mixture was stirred at room temperature for 30 minutes and the reaction was quenched by slowly adding 25 g of ice. The quenched reaction mixture was diluted with 50 ml of ether and 25 ml of water and the layers were separated. The organic layer was dried over magnesium sulfate and concentrated in vacuo to afford 2.03 g (98%) of the title compound as a light-sensitive solid. The dimethyl titanocene could be stored as a solution in toluene at 0° C. for at least 2 weeks without apparent chemical degradation. $^1$H NMR (200 MHz, CDCl$_3$) δ−0.15 (6H, s), 6.06 (10H, s).
Step B 4-Benzyl-2-(R)-(1-(3,5-bis(trifluoromethyl)phenyl) ethenyloxy)-3-(S)-(4-fluorophenyl) morpholine A solution of the compound of Description 3 (2.50 g, 4.9 mmol) and 2.50 g (12.0 mmol) of dimethyl titanocene (from Step A) in 35 ml of 1:1 v/v THF/toluene was stirred in an oil bath at 80° C. for 16 hours. The reaction mixture was cooled and concentrated in vacuo. Flash chromatography on 150 g of silica gel using 3:1 v/v hexanes/methylene chloride as the eluant afforded 1.71 g (69%) of the title compound as a solid. An analytical sample was obtained via recrystallisation from isopropanol: $^1$H NMR (400 MHz, CDCl$_3$) δ2.42 (1H, dt, J=3.6, 12.0 Hz), 2.90 (1H, app d, J=12.0 Hz), 2.91 (1H, d, J=13.6 Hz), 3.62–3.66 (1H, m), 3.72 (1H, d, J=2.6 Hz), 3.94 (1H, d, J=13.6 Hz), 4.09 (1H, dt, J=2.4, 12.0 Hz), 4.75 (1H, d, J=3.2 Hz), 4.82 (1H, d, J=3.2 Hz), 5.32 (1H, d, J=2.6 Hz), 7.09 (2H, t, J=8.8 Hz), 7.24–7.33 (5H, m), 7.58–7.62 (2H, m), 7.80 (1H, s), 7.90 (2H, s); MS (FAB) 526 (M+H, 75%), 270 (100%). Analysis Calcd. for C$_{27}$H$_{22}$F$_7$NO$_2$: C, 61.72; H, 4.22; N, 2.67; F, 25.31. Found: C, 61.79; H, 4.10; N, 2.65; F, 25.27%

DESCRIPTION 5

2-(R)-(1-(R)-(3,5-Bis(trifluoromethyl)phenyl) ethoxy)-3-(S)-(4-fluorophenyl) morpholine The compound of Description 4 (4.0 g) was dissolved in ethyl acetate (50 ml) and isopropanol (16 ml). To this solution was added palladium on charcoal (1.5 g) and the mixture was hydrogenated at 40 psi for 36 h. The catalyst was removed by filtration through Celite and the solvents were removed in vacuo. The residue was purified by flash chromatography on silica using 100% ethyl acetate and then 1–10% methanol in ethyl acetate. This afforded isomer A 500mg (15%) and isomer B 2.6 g (80%) as clear oils - isomer B crystallised on standing. For the title compound: $^1$H NMR (400 MHz, CDCl$_3$) δ1.16 (3H, d, J=6.8 Hz), 1.80 (1H, br s), 3.13 (1H, dd, J=3.2, 12.4 Hz), 3.23 (1H, dt, J=3.6, 12.4 Hz), 3.63 (1H, dd, J=2.4, 11.2 Hz), 4.01 (1H, d, J=2.4 Hz), 4.13 (1H, dt, J=3.2, 12.0 Hz), 4.42 (1H, d, J=2.4 Hz), 4.19 (1H, q, J=6.8 Hz), 7.04–7.09 (2H, m), 7.27–7.40 (4H, m), 7.73 (1H, s); MS (FAB) 438 (M+H, 75%), 180 (100%).

EXAMPLE 1

2-(R)-(1-(R)-(3,5-Bis(trifluoromethyl)phenyl) ethoxy)-3-(S)-(4-fluorophenyl)-4-(1,2 4-triazol-3-yl) methylmorpholine A solution of the compound of Description 5 (3.77 g) and potassium carbonate (3.59 g) in dry dimethylformamide (7 ml) was stirred at room temperature for 10 min. N-Formyl-2-chloroacetamidrazone (prepared according to Yanagisawa L, J. Med Chem. 71, 1984, 27, 849) was added and the reaction mixture was heated at 60° C. for 1 hour. The temperature was then increased to 140° C. for 2 h. The mixture was cooled and partitioned between ethyl acetate and water and the organic phase was washed with water, brine, dried (MgSO$_4$) and evaporated to give a brown oil. The residue was purified by chromatography on silica using 1–5% methanol in dichloromethane. This afforded the product as a white foam (2.99 g). $^1$H NMR (360 MHz, DMSO) δ8.25 (1H, s), 7.85 (1H, s), 7.50 (2H, t), 7.37 (2H, s), 7.11 (2H, t, J=9.0 Hz), 4.93 (1H, q, J=6.6 Hz), 4.32 (1H, d, J=2.8 Hz), 4.09 (1H, dt, J=11.5 Hz), 3.63 (1H, d, J=14.1 Hz), 3.59 (1H, d, J=3.0 Hz), 3.17 (1H, d, J=14.0 Hz), 2.49 (1H, dt, J=15.7 Hz), 1.36 (3H, d, J=6.6 Hz). MS (CI$^+$) m/z 519. Analysis Calcd. for C$_{23}$H$_{19}$F$_7$N$_4$O$_2$: C, 53.29; H, 4.08; N, 10.81; Found: C, 52.92; H, 3.94; N, 10.33%

EXAMPLE 2

2-(R)-(1-(R)-(3,5-Bis(trifluoromethyl)phenyl) ethoxy)-3-(S)-(4-fluorophenyl)-4-(1,3-imidazol-4-yl) methylmorpholine Step A 4-Hydroxymethyl-N-(p-toluenesulfonyl)imidazole 4-Hydroxymethylimidazole hydrochloride (10 g) was suspended in dichloromethane (200 ml). p-Toluenesulfonyl chloride (15.58 g) was added and triethylamine (25.8 ml) was added dropwise to the stirred reaction mixture which was allowed to stir at room temperature overnight. The mixture was washed with water (2×100 ml) and brine (1×100 ml) and the organic layer was dried and evaporated to leave a clear oil which was recrystallised from ethyl acetate/hexane to afford a white crystalline solid (15 g, 80%). $^1$H NMR (360 MHz, CDCl$_3$) δ2.44 (3H, s), 4.55 (2H, s), 7.21 (1H, s), 7.35 (2H, d, J=8.0 Hz), 7.62 (2H, d, J=8.0 Hz), 7.98 (1H, s). MS (CI$^+$) m/z 253 (M+H, 100%).

Step B (N-P-Toluenesulfonyl)imidazol-2-yl)methyl methanesulfonate

The alcohol described in (a) above (1 g) was dissolved in dichloromethane (15 ml) and the solution was cooled in an ice-methanol bath. Triethylamine (0.4 g) was added dropwise in dichloromethane (1 ml) followed by methanesulfonyl chloride (0.45 g). The mixture was washed with water (2×10 ml) and brine (1×10 ml) and the organic layer was dried and evaporated to leave a white crystalline powder (1.3 g). This was used in the next reaction without further purification. $^1$H NMR (360 MHz, CDCl$_3$) δ2.45 (3H, s), 3.00 (3H, s), 5.13 (2H, s), 7.39 (2H, d, J=8.0 Hz), 7.40 (1H, s), 7.84 (2H, d, J=8.0 Hz), 8.00 (1H, s). MS (CI$^+$) m/z 267 ((M-CH$_3$O)$^+$, 30%).

Step C 2-(R)-(1-(R)-(3,5-Bis(trifluoromethyl)phenyl) ethoxy)-3-(S)-(4-5 fluorophenyl)-4-(N-p-toluenesulfonyl- 1,3-imidazol-4-yl) methylmorpholine The compound of Description 5 (500 mg), potassium carbonate (474 mg) and the mesylate referred to in (b) above (432 mg) were suspended in N,N-dimethylformamide (5 ml) and the resulting mixture was stirred at 60° C. for 4 hr. The mixture was cooled and diluted with water (50 ml). The 10 mixture was extracted with ethyl acetate (3×20 ml) and the organic layer was washed with brine, dried (MgSO$_4$) and evaporated. The residue was purified by column chromatography on silica using 30% ethyl acetate in petrol as eluant to afford the product (515 mg, 70%) as a white crystalline solid. MS (CI$^+$) m/z 672 ((M+H)$^+$, 100%).

Step D 2-(R)-(1-(R)-(3,5-Bis(trifluoromethylphenyl)ethoxy) -3-(S)-(4-fluorophenyl)-4-(1,3-imidazol-4-yl) methylmorpholine The compound referred to in (c) above (500 mg) was deprotected by treatment with ethereal hydrogen chloride. The mixture was evaporated in vacuo and the residue was triturated with ether several times and the ethereal washings were decanted to remove the liberated p-toluenesulfonyl chloride. The residual product was treated with aqueous potassium carbonate to liberate the free base and this was extracted with ethyl acetate. The organic layer was washed with water, brine, dried (MgSO$_4$) and evaporated in vacuo. The residue was purified by column chromatography on silica using 2–6% methanol in dichloromethane as eluant. $^1$H NMR (250 MHz, CDCl$_3$) δ1.45 (3H, d, J=7.0 Hz), 2.55 (1H, dt, J=12.0, 3.0 Hz), 2.96 (1H, d, J=12.0 Hz), 3.18 (1H, d, J=14.0 Hz), 3.41 (1H, d, J=3.0 Hz), 3.67 (1H, m), 3.71 (1H, d, J=14.0 Hz), 4.25 (1H, m), 4.31 (1H, d, J=3.0 Hz), 4.86 (1H, q, J=7.0 Hz), 6.81 (1H, s), 7.05 (2H, t, J=8.0 Hz), 7.13 (2H, s), 7.42 (2H, br s), 7.63 (1H, s), 7.68 (1H, s). MS (CI$^+$) m/z 518 ((M+H)$^+$, 20%).

The following examples illustrate pharmaceutical compositions according to the invention.

EXAMPLE 3A
Tablets containing 1–25 mg of compound

|  | Amount mg |  |  |
|---|---|---|---|
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 3B
Tablets containing 26–100 mg of compound

|  | Amount mg |  |  |
|---|---|---|---|
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 4
Parenteral injection

|  | Amount mg |
|---|---|
| Compound of formula (I) | 1 to 100 mg |
| Citric Acid Monohydrate | 0.75 mg |
| Sodium Phosphate | 4.5 mg |
| Sodium Chloride | 9 mg |
| Water for injection | to 10 ml |

The sodium phosphate, citric acid monohydrate and sodium chloride are dissolved in a portion of the water. The compound of formula (I) is dissolved or suspended in the solution and made up to volume.

EXAMPLE 5
Topical formulation

|  | Amount mg |
|---|---|
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

EXAMPLE 6A
(Surface-Active Agent) Injection Formulation

|  |  |
|---|---|
| Compound of formula (I) | up to 10 mg/kg |
| Tween 80 ™ | up to 2.5% |

[in 5% aqueous mannitol (isotonic)]

The compound of formula (I) is dissolved directly in a solution of the commercially available Tween 80™ (polyoxyethylenesorbitan monooleate) and 5% aqueous mannitol (isotonic).

EXAMPLE 6B
(Emulsion) Injection Formulation

|  |  |
|---|---|
| Compound of formula (I) Intralipid ™ (10–20%) | up to 30 mg/ml |

The compound of formula (I) is dissolved directly in the commercially available Intralipid ™ (10 or 20%) to form an emulsion.

EXAMPLE 6C
Alternative (Emulsion) Injectable Formulation

|  | Amount |
|---|---|
| Compound of formula (I) | 0.1–10 mg |
| Soybean oil | 100 mg |
| Egg phospholipid | 6 mg |
| Glycerol | 22 mg |
| Water for injection | to 1 ml |

All materials are sterilized and pyrogen free. The compound of formula (I) is dissolved in soybean oil. An emulsion is then formed by mining this solution with the egg phospholipid, glycerol and water. The emulsion is then sealed in sterile vials.

We claim:

1. A compound of formula (I), or a pharmaceutically acceptable salt or prodrug thereof:

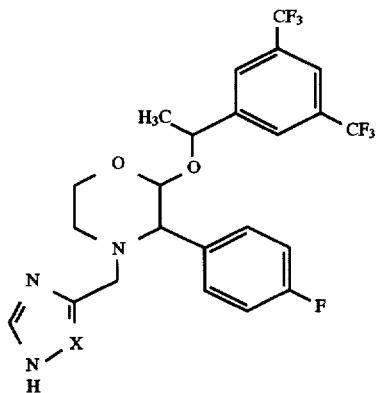

wherein

X is N.

2. The compound: 2-(R)-(1-(R)-(3,5-Bis(trifluoromethyl) phenyl)ethoxy)-3-(S)-(4-fluorophenyl)-4-(1,2,4-triazol-3-yl)methylmorpholine;

or a pharmaceutically acceptable salt or prodrug thereof.

3. A pharmaceutical composition comprising a compound as claimed in claim 1 in association with a pharmaceutically acceptable carrier or excipient.

4. A method for the treatment or prevention of physiological disorders associated with an excess of tachykinins, which method comprises administration to a patient in need thereof of a tachykinin reducing amount of a compound according to claim 1, or a pharmaceutically acceptable salt or prodrug thereof.

5. A method according to claim 4 for the treatment or prevention of pain or inflammation.

6. A method according to claim 4 for the treatment or prevention of migraine.

7. A method according to claim 4 for the treatment or prevention of emesis.

* * * * *